US00PP26259P2

(12) United States Plant Patent
Fell, Jr.

(10) Patent No.: US PP26,259 P2
(45) Date of Patent: Dec. 22, 2015

(54) ***VRIECANTAREA* PLANT NAMED 'JULIETTA'**

(50) Latin Name: *Vriecantarea hybrida*
Varietal Denomination: Julietta

(71) Applicant: David N. Fell, Jr., Waimanalo, HI (US)

(72) Inventor: David N. Fell, Jr., Waimanalo, HI (US)

(73) Assignee: FANTASTIC Gardens Hawaii, Inc, Waimanalo, HI (US)

( * ) Notice: Subject to any disclaimer, the term of this patent is extended or adjusted under 35 U.S.C. 154(b) by 206 days.

(21) Appl. No.: 13/998,472

(22) Filed: Nov. 4, 2013

(51) Int. Cl.
*A01H 5/12* (2006.01)

(52) U.S. Cl.
USPC ..... Plt./370

(58) Field of Classification Search
USPC ..... Plt./370
See application file for complete search history.

*Primary Examiner* — Anne Grunberg
(74) *Attorney, Agent, or Firm* — C. A. Whealy

(57) ABSTRACT

A new and distinct cultivar of Vriecantarea plant named 'Julietta', characterized by its upright and outwardly arching growth habit; glossy dark purple and green-colored leaves; and good interiorscape performance with plants maintaining good leaf color for about six months under moderate light levels.

1 Drawing Sheet

Botanical designation: *Vriecantarea hybrida.*
Cultivar denomination: 'JULIETTA'.

BACKGROUND OF THE INVENTION

The present invention relates to a new and distinct cultivar of *Vriecantarea* plant, botanically known as *Vriecantarea hybrida*, previously known as (*Alcantarea imperialis*× *Vriesea polemanii*)×*Alcantarea vinacolor*, and hereinafter referred to by the name 'Julietta'.

The new *Vriecantarea* plant is a product of a planned breeding program conducted by the Inventor in Hilo, Hawaii. The objective of the breeding program is to create new *Vriecantarea* plants with uniquely colored leaves and good interiorscape performance.

The new *Vriecantarea* plant originated from a self-pollination made by the Inventor in 2009 in Hilo, Hi. of *Vriecantarea hybrida* 'Volcano's Mist', not patented. The new *Vriecantarea* plant was discovered and selected by the Inventor as a single plant within the progeny of the stated self-pollination in a controlled greenhouse environment in Hilo, Hi. in 2010.

Asexual reproduction of the new *Vriecantarea* plant by offsets and micro-propagation in a controlled environment in Hilo, Hi. since 2011 has shown that the unique features of this new *Vriecantarea* plant are stable and reproduced true to type in successive generations.

SUMMARY OF THE INVENTION

Plants of the new *Vriecantarea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Julietta'. These characteristics in combination distinguish 'Julietta' as a new and distinct *Vriecantarea* plant:

1. Upright and outwardly arching growth habit.
2. Glossy dark purple and green-colored leaves.
3. Good interiorscape performance with plants maintaining good leaf color for about six months under moderate light levels.

Plants of the new *Vriecantarea* differ primarily from plants of the parent, 'Volcano's Mist', in the following characteristics:

1. Leaves of plants of the new *Vriecantarea* are more intensely-colored than leaves of plants of 'Volcano's Mist'.
2. Leaves of plants of the new *Vriecantarea* have a thicker waxy cuticle than leaves of plants of 'Volcano's Mist'.

Plants of the new *Vriecantarea* can be compared to plants of unnamed selections of *Alcantarea imperialis* known to the Inventor, not patented. In side-by-side comparisons conducted in Hilo, Hi., plants of the new *Vriecantarea* and the unnamed selections of *Alcantarea imperialis* differed primarily in the following characteristics:

1. Leaves of plants of the new *Vriecantarea* were more intensely-colored than leaves of plants of the unnamed selections of *Alcantarea imperialis.*
2. Leaves of plants of the new *Vriecantarea* had a thicker waxy cuticle than leaves of plants of the unnamed selections of *Alcantarea imperialis.*

BRIEF DESCRIPTION OF THE PHOTOGRAPHS

The accompanying colored photographs illustrate the overall appearance of the new *Vriecantarea* plant showing the colors as true as it is reasonably possible to obtain in colored reproductions of this type. Colors in the photographs may differ slightly from the color values cited in the detailed botanical description which accurately describe the colors of the new *Vriecantarea* plant.

The photograph at the bottom of the sheet is a side perspective view of a typical plant of 'Julietta' grown in a container.

The photograph at the top of the sheet is a top perspective view of a typical plant of 'Julietta'.

DETAILED BOTANICAL DESCRIPTION

The aforementioned photographs and following observations, measurements and values describe plants grown during the summer in 15.25-cm containers in an outdoor nursery in Hilo, Hi. and under cultural practices typical of commercial *Vriecantarea* production. During the production of the plants, day temperatures ranged from 18° C. to 32° C., night temperatures ranged from 12° C. to 25° C. and light levels averaged 18,000 foot-candles. Plants were six months old when the photographs and description were taken. In the following description, color references are made to The Royal Horticultural Society Colour Chart, 2007 Edition, except where general terms of ordinary dictionary significance are used.

Botanical classification: *Vriecantarea hybrida* 'Julietta'.

Parentage: Self-pollination of *Vriecantarea* hybrida 'Volcano's Mist', not patented.

Propagation:

*Type*.—By offsets and by micro-propagation.

*Time to initiate roots, summer*.—About three weeks at 27° C. soil temperatures and 29° C. air temperatures.

*Time to initiate roots, winter*.—About one month at 21° C. soil temperatures and 27° C. air temperatures.

*Time to produce a rooted young plant, summer*.—About three months at 27° C. soil temperatures and 29° C. air temperatures.

*Time to produce a rooted young plant, winter*.—About 100 days at 21° C. soil temperatures and 27° C. air temperatures.

*Root description*.—Medium in thickness, fibrous; white in color.

*Rooting habit*.—Freely branching; medium density.

Plant description:

*Plant and growth habit*.—Upright and outwardly arching growth habit; rosette leaves are erect when young, becoming outwardly arching with development; vigorous growth habit.

*Plant height*.—About 38 cm; with subsequent development, plants achieve a plant height of about 125 cm.

*Plant diameter or spread*.—About 47 cm; with subsequent development, plants achieve a diameter of about 200 cm.

*Internode length*.—About 5 mm.

*Stem texture*.—Smooth, glabrous.

*Stem color*.—Close to 155C.

Leaf description:

*Arrangement*.—Rosette, spiral phyllotaxis; simple; sessile, leaf bases sheathing and clasping the stem.

*Length*.—About 30 cm to 32 cm.

*Width*.—About 8.5 cm.

*Shape*.—Oblong.

*Apex*.—Cuspidate.

*Base*.—Truncate.

*Margin*.—Entire.

*Texture, upper and lower surfaces*.—Smooth, glabrous; leathery, tough; relatively thick waxy cuticle or "bloom", thicker on upper surface.

*Luster, upper and lower surfaces*.—Glossy.

*Venation pattern*.—Parallel.

*Color*.—Youngest leaves, upper and lower surfaces: Close to 146B to 146C; towards the apex, tinted with close to N186C. Basal leaves, upper surface: Mid-section to apex, close to 137A; towards the base, close to 183A to 183B. Basal leaves, lower surface: Towards the apex, close to 147B with random flecking close to 187B; mid-section and towards the base, close to N186A to N186B. Upper leaves, upper surface: Close to N186C; venation, close to N186C. Upper leaves, lower surface: Close to 187A; venation, close to 187A.

Inflorescence description: Inflorescence initiation and development have not been observed on plants of the new *Vriecantarea*.

Temperature tolerance: Plants of the new *Vriecantarea* have been observed to tolerate temperatures ranging from about 4.4° C. to about 46° C.

Interior performance: Plants of the new *Vriecantarea* have been observed to have good postproduction longevity and maintain good leaf coloration under moderate light for about six months under interior conditions.

Disease & pest resistance: Plants of the new *Vriecantarea* have not been observed to be resistant to pathogens and pests common to *Vriecantarea* plants.

It is claimed:

1. A new and distinct *Vriecantarea* plant named 'Julietta' as illustrated and described.

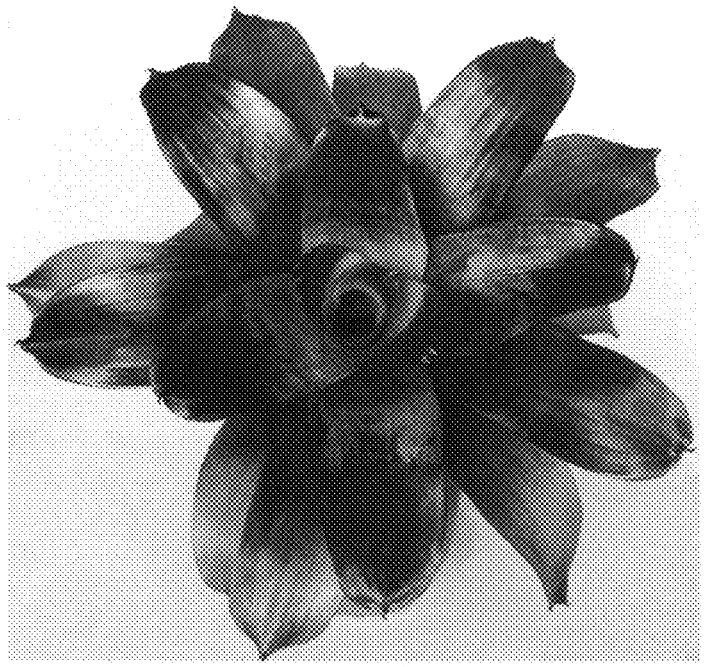
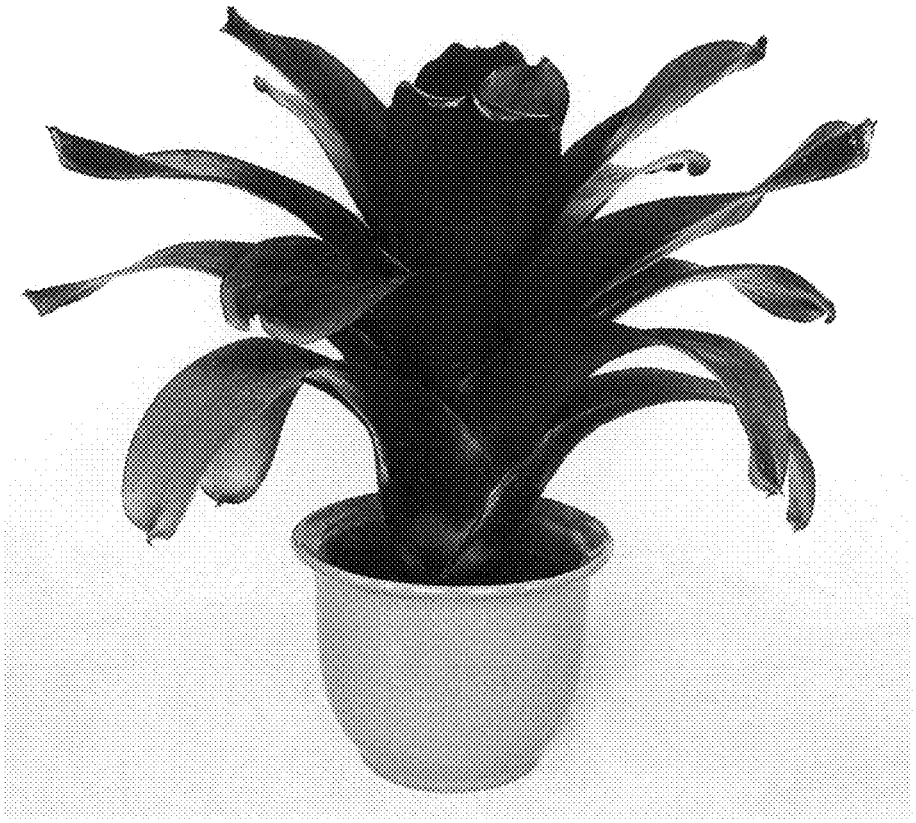

* * * * *